United States Patent [19]

Villa-Real

[11] Patent Number: 4,473,530
[45] Date of Patent: Sep. 25, 1984

[54] COMPACT SANITARY URINALYSIS UNIT

[76] Inventor: Antony-Euclid C. Villa-Real, 2512 Capistrano Ave., Las Vegas, Nev. 89121

[21] Appl. No.: 190,635

[22] Filed: Sep. 24, 1980

[51] Int. Cl.³ .......................................... G01N 33/50
[52] U.S. Cl. ....................... 422/58; 422/61; 422/104; 128/762; 128/771; 73/863.52; 215/6; 215/DIG. 8
[58] Field of Search ........................ 422/61, 58, 59, 60, 422/102, 101, 104; 215/6, DIG. 8; 206/221, 219; 210/927, 518; 73/444, 450, 863.52; 128/762, 771

[56] References Cited

U.S. PATENT DOCUMENTS

| | | | |
|---|---|---|---|
| 2,527,991 | 10/1950 | Greenberg | 206/221 |
| 3,774,455 | 11/1973 | Seidler et al. | 422/56 |
| 3,814,522 | 6/1974 | Clark | 422/102 |
| 3,884,072 | 5/1975 | Cheng | 422/56 |
| 3,924,741 | 12/1975 | Kachur | 215/6 |
| 4,024,952 | 5/1977 | Leitz | 215/6 |
| 4,043,762 | 8/1977 | Olds | 422/104 |
| 4,066,414 | 1/1978 | Selby | 422/102 |
| 4,105,415 | 8/1978 | Lovett | 422/58 |
| 4,125,372 | 11/1978 | Kavai et al. | 422/56 |

FOREIGN PATENT DOCUMENTS

533083 2/1941 United Kingdom ................ 206/221

Primary Examiner—William F. Smith
Attorney, Agent, or Firm—Sughrue, Mion, Zinn, Macpeak and Seas

[57] ABSTRACT

The disclosure relates to a device for performing routine urinalysis. A closed integrated system enables the user to do the important variety of tests and steps during each procedure, thereby greatly minimizing the exposure of the user to the undesired contamination from the urine specimen being tested and facilitating the performance of the testing procedure under a shorter timeframe and initiating lesser laboratory wares expenditure. The device is comprised of a clear and transparent tubular container, subdivided into a larger main longitudinal chamber integrated with two adjacent smaller longitudinal chambers therein. One of the smaller longitudinal chambers being calibrated to the equivalence of the routinely accepted specific gravity urinometer (hydrometer) and, inside this chamber is a small flotation component for determining the specific gravity of the urine specimen trapped therein. The second smaller longitudinal chamber contains a built-in chemical reagent strip so that upon the entrance of urine specimen, color changes in the strip will result in determining the quali-quantitative approximate levels of ph, protein, glucose, bilirubin, ketones, free hemoglobin, and urobilinogen found in each urine specimen. The device has a thin flattened double-walled cul-de-sac-like lower section to accommodate the urine sediments after centrifugation providing a means for the microscopist to investigate the formed constituents of the urine sediment under a microscope. A special cap has a factory placed powdered stain which can be released into the urine specimen contained in the larger main chamber, just before centrifugation in order to bring about greater visual contrast of the various constituent elements found in each particular specimen's urinary sediment to effect better microscopic analysis of the urine. The entire compact sanitary urinalysis unit is made to be disposable after a singular use.

1 Claim, 16 Drawing Figures

COMPACT SANITARY URINALYSIS UNIT

BACKGROUND OF THE INVENTION

In the current practice of routine urinalysis testing which is done in most hospitals, doctors' offices and commercial medical laboratories, there are a number of disadvantages which can be eliminated. The disadvantages are as follows:

1. It involves a longer time-frame for the performance of each individual routine urinalysis testing procedure because of the many separate time-consuming steps involved, thereby delaying the important reporting of the test results to the clinician.

2. In cases wherein there is a multitude of urine specimens from various patients or individuals being analyzed, accentuated by the input of incoming emergency urine specimens to be tested at various intervals, there is a resultant greater confusion factor and tension on the part of the technologist, nurse or doctor thus increasing the potential errors in reporting.

3. There are more laboratory wares that are used in a non-integrated method, thereby resulting in more cost factors incurred in the laboratory.

4. Because of the longer time-frame involved in the performance of many batches of urine specimens during the day, the eventual collective time-waste factor on the part of the testers account for a greater man-hours loss during the months and years, resulting in much higher expenses to the laboratory owner.

5. Due to the exposure of scattered chemistry test strips that have been dipped into each individual urine specimen for the determination of the levels of free hemoglobin, protein, ketones, ph factor, bilirubin, and glucose, (plus a seventh segment for urobilinogen in some chemistry reagent strips depending upon the need and availability) there results in the undesired spread of contaminating infectious agents such as the virus of infectious hepatitis and other infectious germs predisposing the laboratory personnel to diseases.

This invention presents a better method and device to solve the disadvantages above.

SUMMARY OF THE INVENTION

The present invention generally relates to a method and equipment for routine urinalysis testing, and more particularly to a new innovative method and device which integrates the various important urinalysis testing procedures and wares in the form of a more sanitary compact urinalysis testing unit.

One object of the present invention is therefore to provide an economical integrated urinalysis testing unit that has the capability of eliminating the time-consuming separate steps in the performance of routine urinalysis testing.

Another object of the present invention is to provide a closed system wherein the various steps or stages in the performance of routine urinalysis testing can be undertaken with minimal exposure of the testers to contaminating agents of infectious hepatitis and other forms of infectious diseases that can endanger the health tea and widen the foci of infection predisposing more individuals to these diseases.

And yet another object of the instant invention is to provide a better method and systematic device that is simple to use and at the same time effect the curtailment of the error-factors that may result due to the confusion and tension of the part of the technologist, nurse or doctor as a result of their performance of the various separate steps of routine urinalysis testing that is widely practiced as current urinalysis techniques.

And still a further object of the instant invention is to provide a new method and systematic device containing three longitudinal chambers, namely a larger main longitudinal chamber, and two adjacent smaller longitudinal chambers.

And yet an additional object of the instant invention is to provide a clear and transparent device enabling the tester to visually observe the state of clarity, turbidity, cloudiness or haziness of the urine specimen content, and to visually verify the intensity and differentiation of urine color.

A still further object of the present invention is to provide a device having a smaller longitudinal chamber containing a built-in chemistry reagent strip so that upon flooding of the said chamber by the incoming urine specimen, color changes in the chemistry reagent strip can be brought about to determine the levels of concentration of such entities such as ph factor, protein, bilirubin, urobilinogen, ketones, glucose, and free hemoglobin, without outside exposure of the said reagent strip.

A further object of the instant invention is to provide a unique device for accommodating the individual's urine specimen into the tube wherein the larger main chamber has no fluid communication with the two adjacent smaller longitudinal chambers integrated in the device on account of a longitudinally running non-porous wall separation so that during and after centrifugation of the urine contained inside the said main chamber, there will be no possible transfer of some molecules or bits and pieces of dislodged chemicals from the built-in chemistry reagent test strip contained in the test strip chamber that may contribute as artifacts adulterating the sediments that are collected at the bottom portion of the double walled microscopic area of the device.

Another further object of the present invention is to provide a smaller longitudinal chamber known as the specific gravity chamber having exterior surface calibrations for the determination of the urine's specific gravity in coordination with a flotation component contained inside the said chamber.

And still another object of the present invention is to provide a common wall between the two smaller longitudinal chambers, said wall having perforations to provide fluidic transfer between each other.

And still a further object of the present invention is to provide a cap having a built-in powdered stain that can be stored inside said cap for long periods of time prior to use, and releasable into the main chamber just before centrifugation of the urine by a simple rotation of said cap; said stain to be used to effect microscopic examination.

Another further object of the present invention is to provide a double walled clear and transparent flattened bottom portion to accommodate the urinary sediments during and after centrifugation so as to allow the microscopist to properly analyze the formed constituents of the urine specimen, without having to transfer its sediment into a separate specimen glass slide in combination with a transparent cover slip.

A further object of the present invention is to provide a factory pre-printed or pre-etched gridded area at the top face of the thin flattened double-walled cul-de-sac-like and microscopic area in order to aid the microscopist in quantitatively estimating the concentration of the formed elements of the urinary sediment such as pus cells, red blood cells, white blood cells, epithilial cells, casts, mucous threads, cylindroids, bacteria, yeast, parasites, glitter cells, crystals, amorphous material, etc.

A still further object of the present invention is to provide a protective sheath material which can conform with the configuration of the thin double walled, flattened cul-de-sac-like sedimentation and microscopic area at the bottom of the device to prevent the breakage of the latter before, during and after centrifugation.

DETAILED DESCRIPTION OF THE ILLUSTRATIVE DRAWINGS

Figures 1, 2:
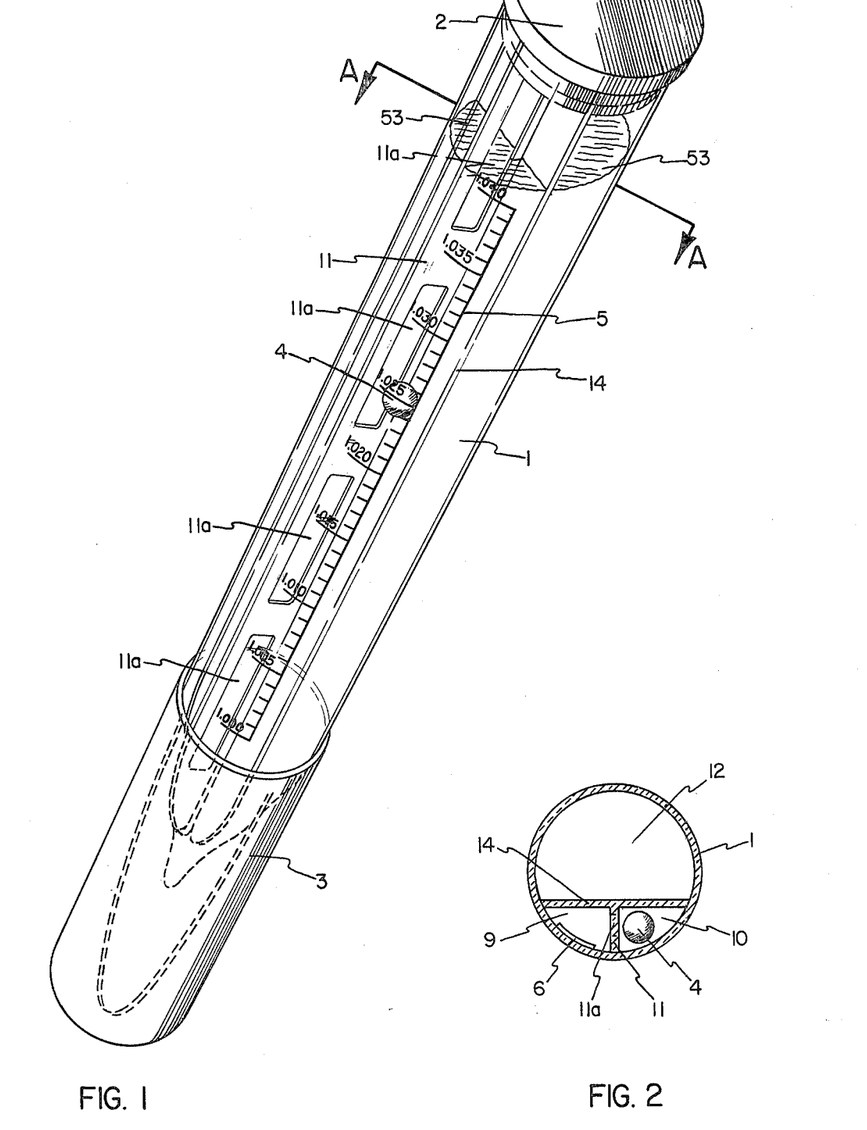
FIG. 1 is an enlarged perspective view of the urinalysis tube of the instant invention.
FIG. 2 is an enlarged cross-sectional view of the urinalysis tube of FIG. 1 taken along the line-and-arrow combination A—A.

There is shown in FIG. 1, the Sanitary Compact Urinalysis tube 1 of the present invention. Sealing the open end of the tube is a rubber cap 2; at the other end of the said tube is a protective sheath 3; to be hereinafter described. The tube 1 is divided into three chambers by walls 11 and 14, said walls forming a longitudinally running T-shaped structure as seen in FIG. 2 which includes a larger main chamber 12, the specific gravity chamber 10 and the test strip chamber 9. Fluid communications between the smaller specific gravity chamber 10 and the test strip chamber 9 is made possible by structural openings 11a so that the urine contents from chamber 9 can transfer to chamber 10 and vice-versa and when enough urine contents are placed in the tube, as illustrated in urine level 53 of FIG. 1, the specific gravity flotation component 4 automatically gets buoyed to a certain level relative to the specific gravity calibrations 5, printed or etched at the outer surface of the specific gravity chamber 10. The height reached by the specific gravity flotation component 4 in relation to the labeled specific gravity calibrations 5 which is shown to be illustrated with equally spaced hair-like markings from the lowest reading of 1.000 to 1.040, is regarded as the specific gravity of that particular urine specimen. For convenience, it is preferable that the weight and the buoyancy factor of the said flotation component 4 should be reading 1.000 at the flotation component's largest diameter when the said flotation component is tested with the normally accepted water. The specific gravity of each particular urine specimen is read by the tester when the specific gravity flotation component 4 settles to its highest point in relation to the specific gravity calibrations 5. The reading of the specific gravity should be made by the tester in a preferably vertical position of the urinalysis tube containing the urine sample and that the largest diameter of the flotation component is matched visually by the tester against the nearest hair-like markings of the calibration. The calibrations for specific gravity are equally spaced in increments or decrements of 0.001. The broken lines at the bottom of the device indicate the structural framework of the device covered by protective sheath 3. The openings 11a shown in FIG. 1 are a series of rectangular equally spaced holes cut across wall 11. Looking in the direction of line A—A, a cross section of the said urinalysis tube is illustrated in FIG. 2 as has already been previously discussed. In addition to the already described chambers 12, 10, and 9 including walls 14 and 11 and openings 11a between chambers 9 and 10 there is found test strip 6 which is shown in the test strip chamber 9 and the flotation component 4 shown inside the specific gravity chamber 10.

Figure 3:
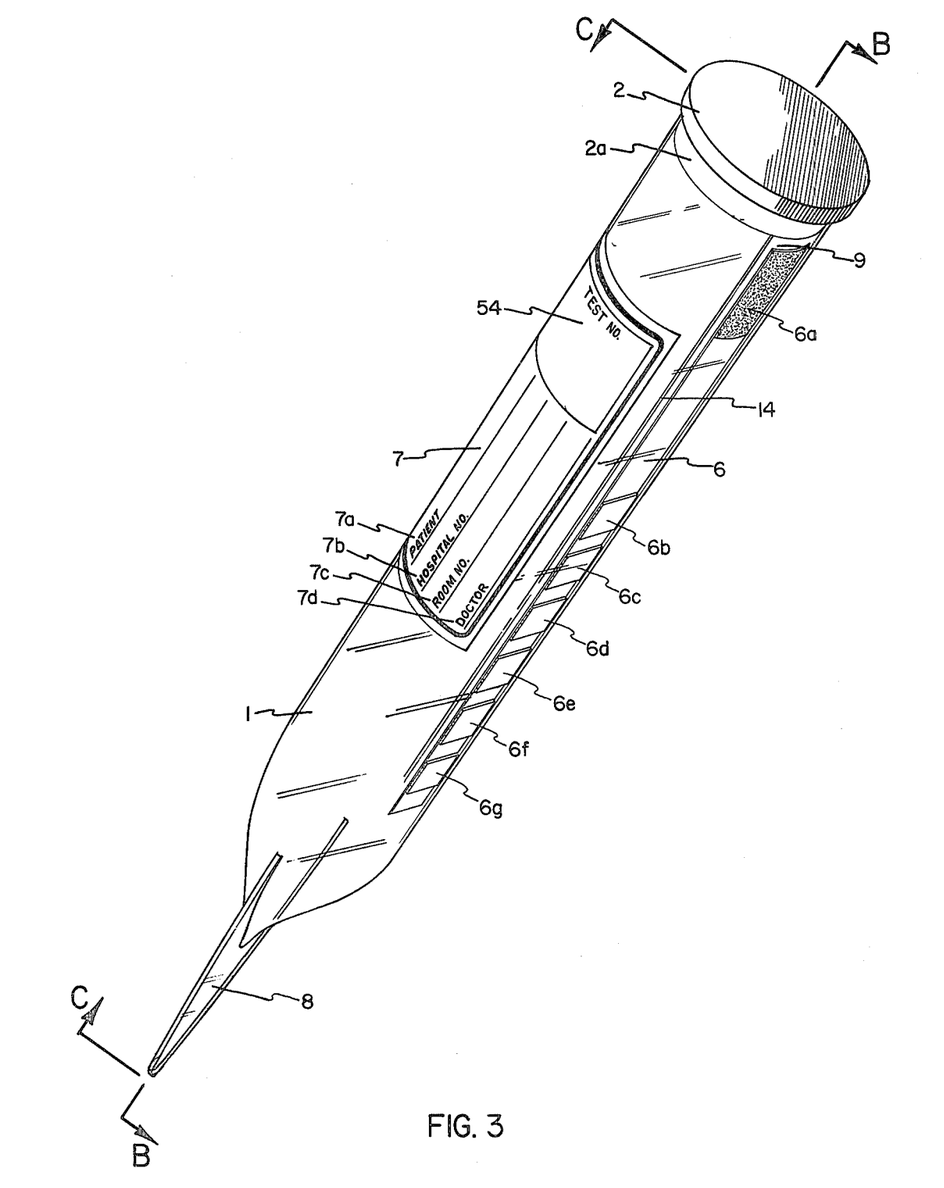
FIG. 3 is an enlarged perspective view of the urinalysis tube of FIG. 1 showing an opposite side of the tube and the protective sheath removed.
Figure 4:
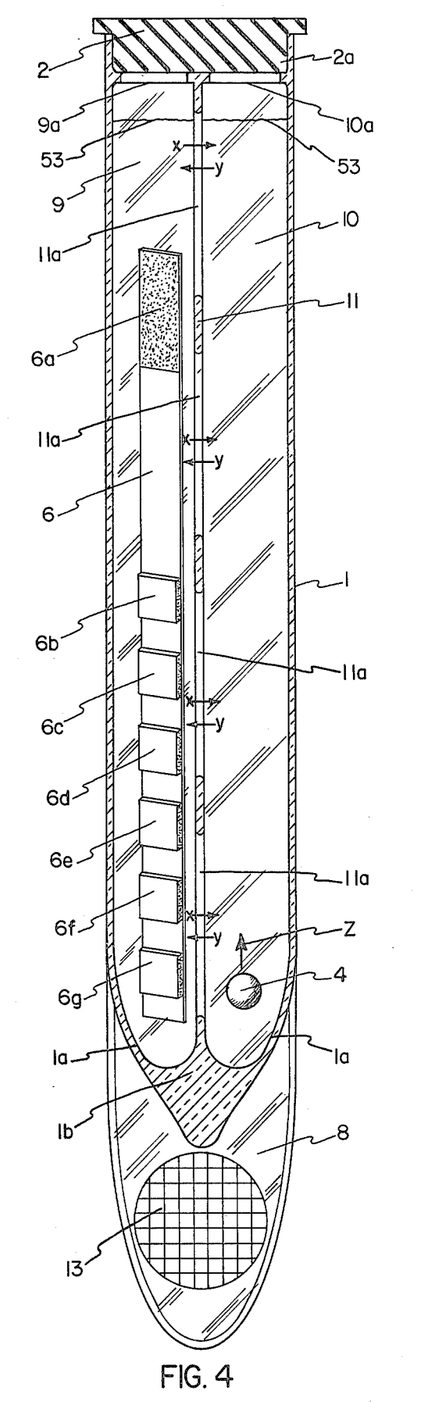
FIG. 4 is an enlarged cross-sectional view of the urinalysis tube of FIG. 3 taken along the line-and-arrow combination B—B and showing the chemistry reagent strip, and the specific gravity flotation component and the urine specimen level just for illustrative clarification.
Figure 15:
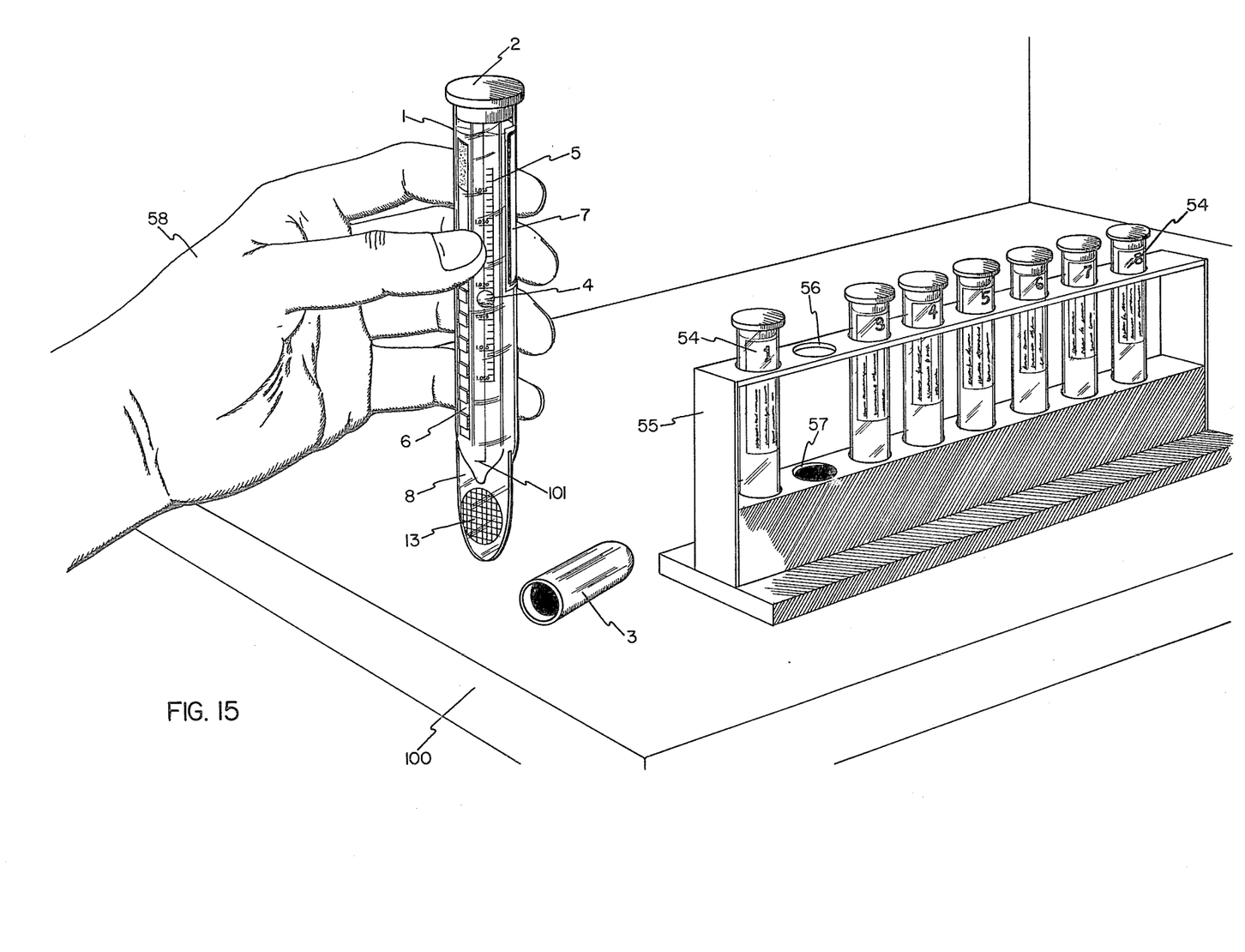
FIG. 15 is a reduced perspective view showing the present device as seen in FIG. 1 being held by the left hand and with the protective sheath removed from the bottom section of the device; said sheath is shown on top of a table; also a series of urinalysis test tubes of the present invention arranged in an orderly fashion are illustrated in perspective view and standing in a vertical position in a urinalysis tube rack shown on the same laboratory table top.

In FIG. 3 the same tube of FIG. 1 is illustrated in perspective view, but this time the protective sheath 3 has been removed, thus exposing the thin flattened one-piece double walled cul-de-sac-like urine sediment area 8 sealed at the external edges; said area being reserved for the microscopic analysis of the centrifuged urinary sediments. In this drawing, the tube of FIG. 1 has been rotated in a counter clock-wise fashion, thus exposing the factory installed information label 7 which illustrates the fundamental information needed for each specimen such as 7a for PATIENT, 7b for HOSPITAL NUMBER, 7c for ROOM NUMBER, and 7d for DOCTOR. Integrated with the same label 7 is space 54 of the label for TEST NUMBER, printed horizontally across the label so that when a series of tubes are aligned in a vertical position in a urine specimen tube rack 55 as shown in FIG. 15, the test numbers can easily be recognized by the doctor, nurse, or technologist performing the urinalysis testing procedure. In this position of tube rotation, the chemical reagent test strip 6 is clearly shown internally located and running longitudinally downwards along the test strip chamber 9. The test strip is shown to have been factory glued or attached to the internal surface of the test strip chamber 9 by means of the adhesive portion 6a of the test strip. Visible to the tester are the various segments of the chemical reagent strips such as 6b, 6c, 6d, 6e, 6f, and 6g which represent the chemical reagents specifically for the various qualiquantative determination of such important chemistry tests as ph factor, protein, glucose, hemoglobin, bilirubin, and ketones. Once the chamber 9 has been flooded with urine specimen, and left alone for a short while, color changes in each individual chemical reagent strip segments can be brought about, and then, the tester can readily see the color changes in the various said reagent segments by just viewing thru the transparent tube wall without exposing or handling the said test strip. Looking in the direction of cross-section arrows B—B, of FIG. 3, we see in FIG. 4, its cross-sectional drawing illustrating the cap 2 with its gripping portion 2a engaged in the upper internal lip of tube 1. Chamber 9 which is the test strip chamber is also shown with its upper opening 9a, inside the said chamber is shown the flotation component 4 together with urine specimen level 53 only for illustrative purposes in order to show how the flotation component 4 floats in an upward direction as indicated by arrow Z. The same test strip 6 including all the different reagent segments 6b, 6c, 6d, 6e, 6f, and 6g and the adhesive component 6a are collectively shown for clarification purposes only including the urine specimen level 53 shown inside chamber 9. The wall 11 separates the chambers 9 and 10 and the four openings 11a are shown in fluid communication as indicated by arrows X and Y. Toward the lower portion of the tube 1, is the internal sloping areas 1a of the structure; 1b is the cross section of the solid glass or plastic material of tube 1 as a result of the sloping. Also shown in FIG. 4 is the top view of the thin double wall flattened sedimentation area 8 and the grid-like markings 13 for better microscopic estimation of such important elements such as pus cells, red blood cells, white blood cells, glitter cells, epithilial cells, mucous threads, cylindroids, casts, amorphous materials, crystals of various kinds, bacteria, parasites like trichonomas vaginalis, yeast cells, ovas, spermatozoa, etc. Since the lower section of the device is not affected by the cross sectioning of arrows B—B of FIG. 3, only the top plan view of the said lower section of the tube is shown without cross hatchings.

Figure 5:
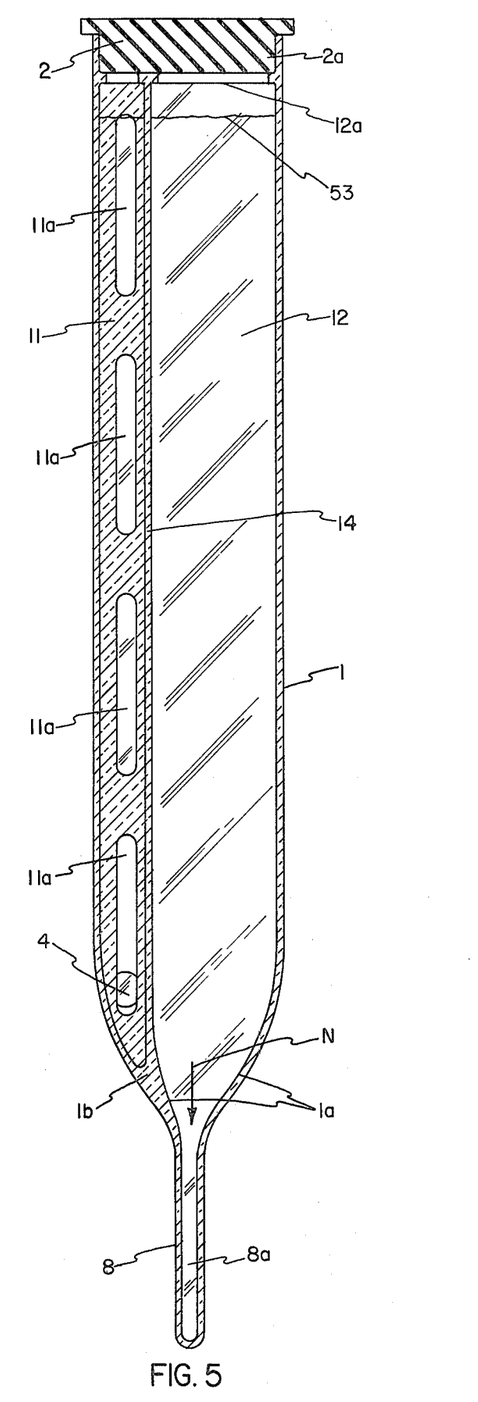
FIG. 5 is an enlarged cross-sectional view of the urinalyis tube of FIG. 3 taken along the line-and-arrow combination C—C; also shown is the specific gravity flotation component trapped inside one of the smaller longitudinal chambers. The urine specimen level is illustrated only for better clarification.

In FIG. 5 we see a cross sectional view of the urinalysis tube including a cap as shown in FIG. 3 taken from line-and-arrow combination C—C of FIG. 3. The cap 2 with its gripping portion 2a is shown in engaging relationship with the upper portion of the tube. Main chamber 12 is shown with its uppermost opening 12a; wall 11 is shown with its equally spaced wall openings 11a, and at the lower portion of the bottom wall opening 11a can be seen part of the specific gravity flotation component 4; wall 14 which separates the main chamber from the two smaller chamber is shown. Toward the lower part of the tube can be seen internal sloping portions 1a which facilitate the accumulation of the urine sediments during centrifugation toward the thin flattened double wall cul-de-sac-like sedimentation collection area 8a, bordered by the side sectional walls of the sedimentation area 8. Arrow N is the direction of the sediment flow as the urine specimen is being centrifuged at a certain pre-selected optimal r.p.m. With this particular configuration of the said sedimentation area, it will require a much shorter time-frame for centrifugation as compared to the time-factor involved in the centrifugation of urine specimens contained inside the commonly used urine centrifuge tubes. This is because of the smaller space for accommodating the urine sediments inside the thin flattened sedimentation microscopic area 8a. In this case, such a feature becomes an additional advantage of the device in the performance of routine urinalysis testing. Urine specimen level 53 is shown only for illustrative clarification.

Figure 6:
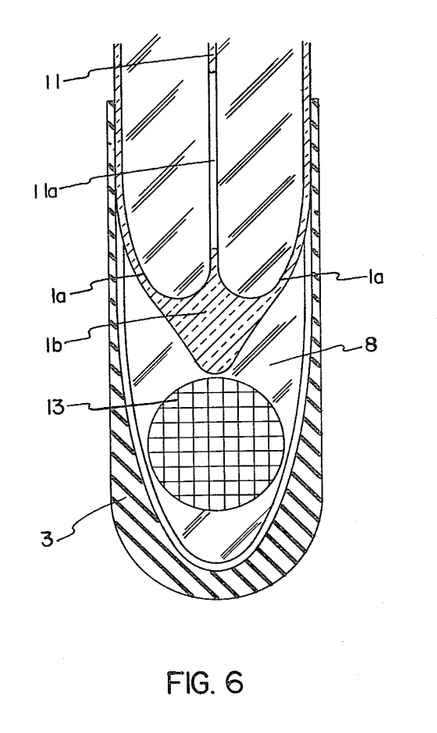
FIG. 6 is an enlarged cross-sectional view representing the bottom portion of the tube of FIG. 4 but surrounded by the protective sheath.

In FIG. 6 is illustrated the lower portion of the device of FIG. 4 but without showing the specific gravity flotation component as well as the chemical reagent strip; however, shown in this drawing is the cross-section of the optimally fitted protective sheath 3 which protects the thin flattened sedimentation area 8 to prevent possible breakage of the said sedimentation area before, during and just after the process of centrifugation. The gridded area 13 has already been described.

Figure 7:
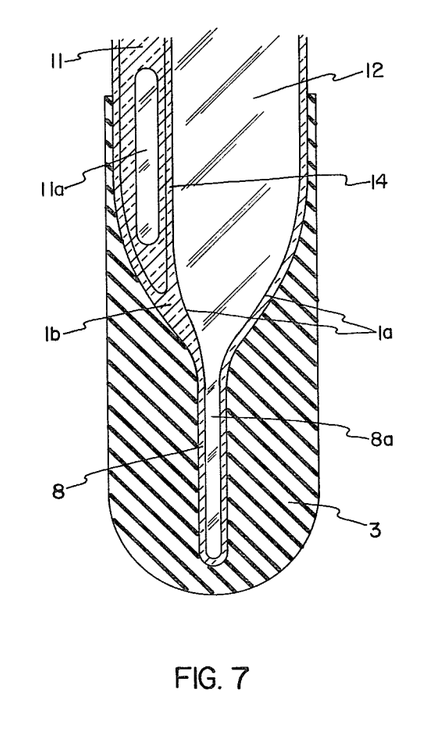
FIG. 7 is an enlarged cross-sectional view representing the bottom portion of FIG. 5 but surrounded by the protective sheath.

In FIG. 7 we see the lower section of FIG. 5 with the protective sheath 3 fitted optimally around 8. In this drawing the flotation component is not shown. All the other numbered parts have already been described in FIG. 5.

Figures 8, 9:
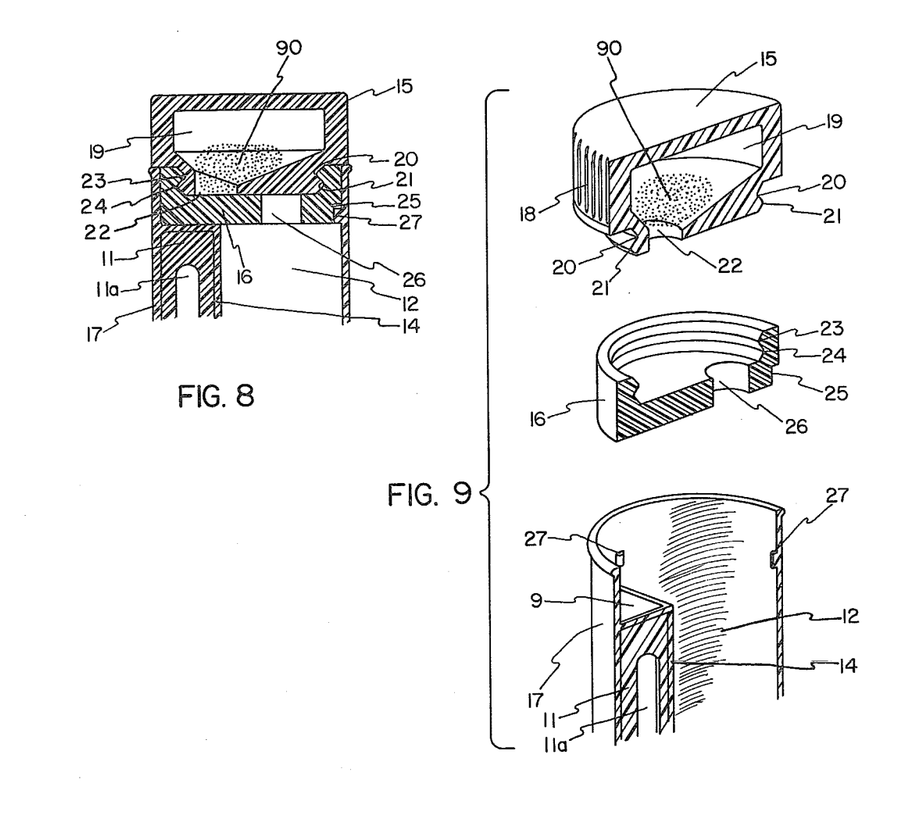
FIG. 8 is an enlarged cross-sectional view of another type of cap for the urinalysis tube of the instant invention; said cap having internally located powdered stain and structural means for storing and releasing said stain.
FIG. 9 is an enlarged exploded perspective and cross-sectional view combination of the cap and tube shown in FIG. 8.

In FIG. 8 we see a cross-section of the upper portion of the urinalysis tube with a special cap; said cap having components specifically structured for the storage of certain powdered staining agents applicable to the urine sediments, and said cap having a means for releasing such staining agents into the main chamber 12 of the tube through an opening 26 when the opening 22 of the upper component of the cap 15 has been aligned with opening 26 of lower component of the cap 16. The staining agent in the form of a powder (for better storage longevity) is stored inside area 19 which is an internal chamber of the upper component 15 of the cap which is rotatable in structural make-up. In the factory, the set-up of the upper component 15 and the lower steady component 16, latched against the internal protrusions 27 of the upper sector of the tube 17 through the matching indentations 25 of the lower component, allows the pre-determined mis-alignment of openings 22 of the upper component of the cap away from the opening 26 of the lower steady component of the cap 16 so that no release of the contained stain 90 can be brought about until the rotatory upper component 15 of the cap has been correctly turned to some optimal degree to allow partial or complete alignment of both openings 22 and 26, at which point the said staining agent 90 can be released into the main chamber 12 just before centrifugation of the urine specimen contained therein. 20 is the inside gripping area of the rotatory component 15; 21 is the outside gripping area of the same rotatory component 15 of the cap, and when coordinated with 23 which is the male circumferentially running ridge of the lower steady component 16 of the cap and 24 which is the female circumferentially running ridge of the lower steady component 16 of the dual piece cap, brings forth the rotational capability of the rotatory component so as to align the opening 22 with opening 26 to allow release of the staining agent contained in chamber 19 into main chamber 12. Wall 11 which separates the two smaller chambers of the tube 17 is shown as well as its wall opening 11a. Wall 14 is shown in cross-sectional view as well; said wall separates the main chamber 12 of tube 17 apart from the two smaller chambers 9 and 10 of FIG. 10.

In FIG. 9 there is shown a perspective exploded half cross-sectional view of the main rotatory component 5 of the cap with all its parts which have already been described in FIG. 8, including the lower steady component 16 of the cap which includes all the already described parts. The tube 17 shows all the previously described parts as well as showing two of the three equally spaced structural protrusions 27 located at the internal wall of the upper sector of tube 17 and higher than walls 11 and 14. The drawing of tube 17 of FIG. 9 which is illustrated in half-sectional view has been taken from line-and-arrow combination E—E of FIG. 10.

Figure 10:
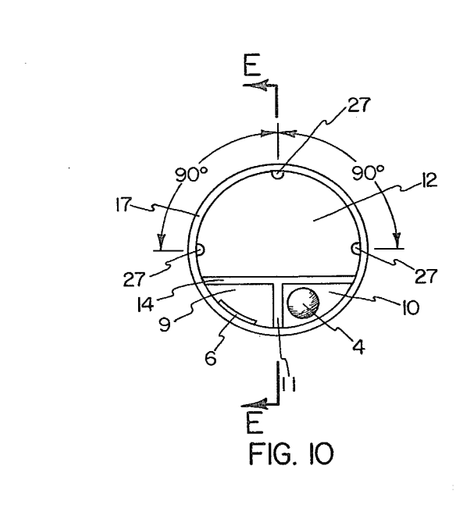
FIG. 10 is an enlarged top elevational view of the urinalysis tube shown in FIGS. 8 and 9.

In FIG. 10 are illustrated the three equally spaced structural protrusions 27. Also shown is the wall 14 which separates the main chamber 12 from the smaller test strip chamber 9 and the specific gravity chamber 10. Wall 11 is also shown between chambers 9 and 10 but 11a is not shown since it is only a top view of the said tube of FIGS. 8 and 9. Test strip 6 is shown engaged at the internal arc-like wall of the test strip chamber 9; flotation component 4 is shown inside specific gravity chamber 10. The two double arrows at the right and at the left side each designated with 90 degree angulations illustrate the correct space relationship between the internal protrusions 27 in relationship to each other in consecutive clock-wise direction as well as in a counter-clock-wise direction as far as their distribution in the main chamber is concerned.

Figure 11:
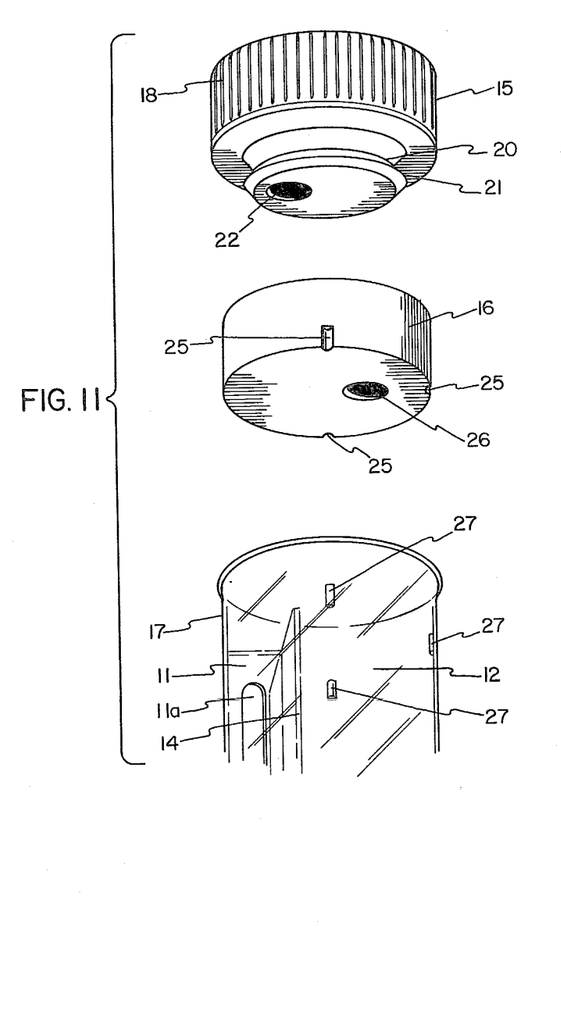
FIG. 11 is an enlarged exploded perspective view emphasizing the lower portion of the cap components and the upper portion of the tube shown in FIG. 9.

In FIG. 11 is shown the exploded perspective views of the rotatory component 15 of the cap, separated from the steady non-rotatory component 16 of the cap, as well as the upper part of the tube 17. This particular perspective view is more inclined to reveal the bottom views of the three components as oppositely illustrated in FIG. 9 which favors more the top inclined perspective views of the same three components. In this FIG. 11 no sectional views of the three components are shown as exposed to the sectional representation in part illustrated in FIG. 9. The gripper portion 18 running vertically and equally spaced all around the outer edge of the rotatory component 15 of the cap is shown including 20 and 21 which have been discussed in the description in FIG. 8. The release opening 22 for the stain contained inside 15 is also clearly shown and the release opening 26 of the non-rotatory component 16 is also clearly shown as well as the three corresponding matching female indentations 25 to match against the three equally spaced structural protrusions 27 of tube 17. All the other structures of tube 17 have already been discussed. It can be clearly understood from this drawing that when the rotatory component 15 becomes optimally engaged with the stationary component 16 of the cap, it is possible to rotate component 15 against component 16 in order to align the opening 22 over the opening 26 to effect the release of the powdered staining agent contained in 15 into the main chamber 12 of tube 17. The reason for having the non-aligned openings 22 and 26 as pre-set in the factory is to prevent the untimely release of the said stain into the main chamber before use. The optimal snug fitting relationship between the upper rotatory component 15 and the stationary component 16 makes it possible for the longer preservation of the potency of the staining agent.

Figure 12:
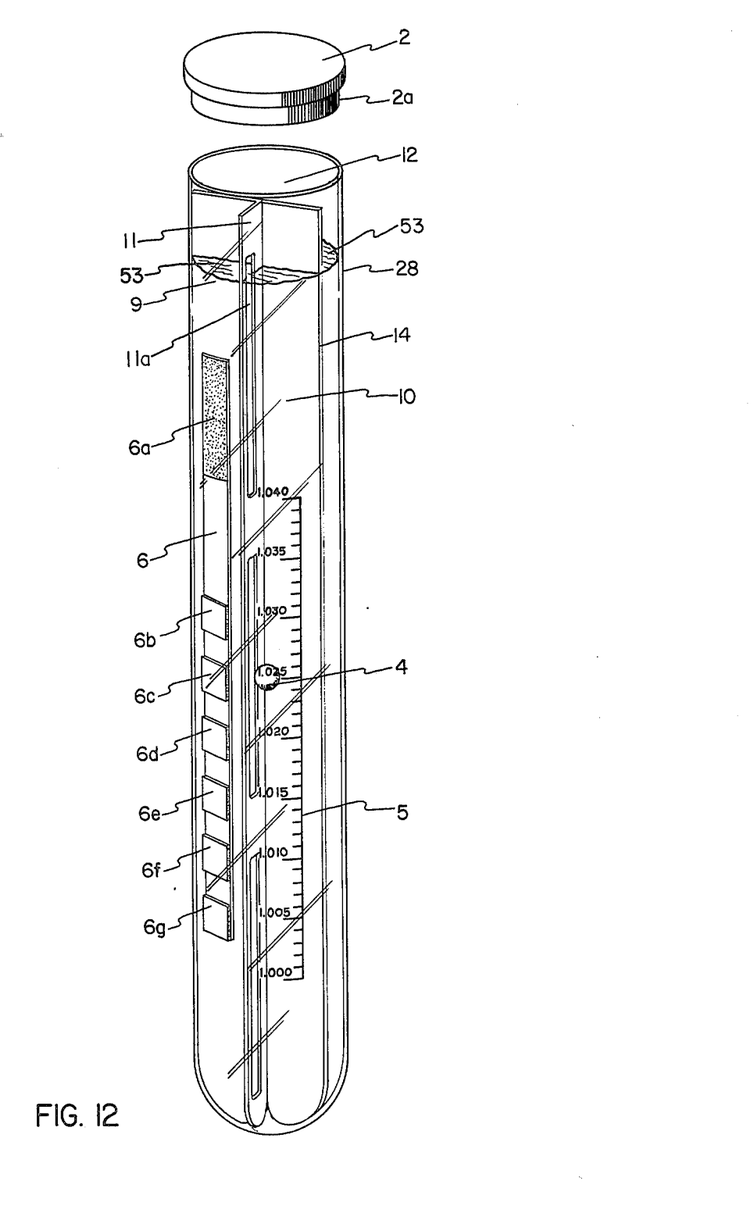
FIG. 12 is an enlarged perspective view of another embodiment of the urinalysis tube without the microscopic examination area.

FIG. 12 fully illustrates another alternative embodiment of the present invention associated with the previously described ordinary cap 2 which has no built-in staining agent. Also shown are: The main chamber 12, the test strip chamber 9, and the specific gravity chamber 10. The main chamber is separated by wall 14 which does not have any direct fluidic transfer with either or both chambers 9 and 10. Wall 11 separates chambers 9 and 10, but because the said wall is provided with wall openings 11a, there is provided direct fluidic transfer between the two chambers thus accentuating the immediate activation of the flotation component 4 to enable the tester to immediately read the specific gravity of the urine in reference to the specific gravity calibrations printed at the outer surface of chamber 10; the said openings 11a also enhances the immediate activation of the necessary color changes in the test strip so that the tester can readily achieve the reading of the various relevant concentrations of the chemicals in the urine being tested by the pre-installed chemical reagent strip 6. The drawing shows the various chemical reagent segments 6b, 6c, 6d, 6e, 6f, and 6g; which are the important ingredients of the test strip. Said test strip is adhesively attached to the internal arc-like wall of the test strip chamber. This embodiment illustrated as an alternative design of the tube provides no sediment examination area for microscopic analysis, therefore the protective sheath as shown in FIGS. 1, 6, and 7 is absent. In order to differentiate this particular tube design, the said tube is labeled 28 differing from the numeral designation of 1 and 17 as in the previously described and illustrated tubes. The urine specimen level 53 is shown at about the proper content height. Because there is no direct fluidic transfer between the main chamber 12 to either or both of the smaller chambers 9 and 10, it is possible that the urine level at the chamber 12 may differ from the collective urine level height of chambers 9 and 10. This FIG. 12 favors the inclined side and top views.

Figures 13, 14:
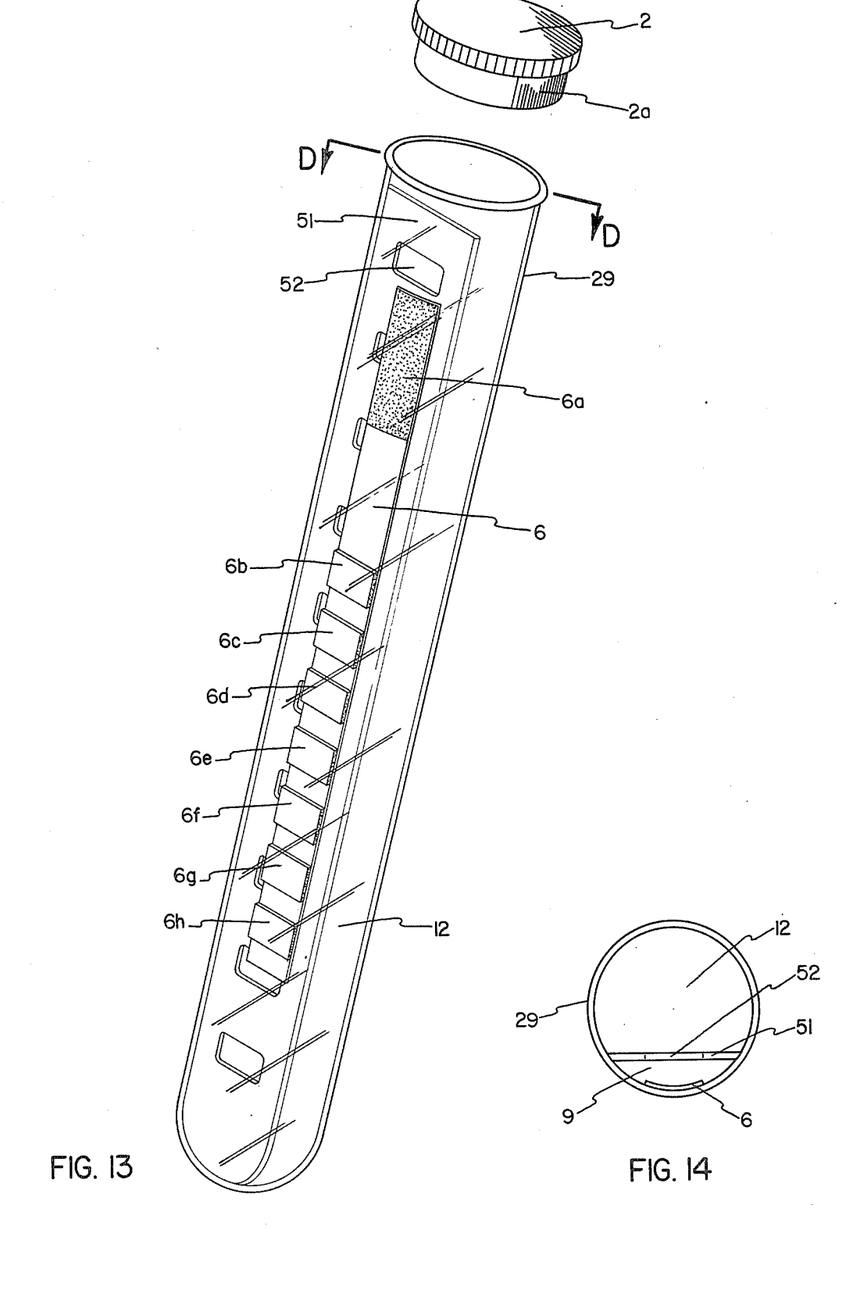
FIG. 13 is an enlarged perspective view of still another urinalysis tube utilizing only two chambers.
FIG. 14 is an enlarged top elevational view of the urinalysis tube shown in FIG. 13 taken along the line-and-arrow combination D—D.

In FIG. 13 there is shown a third alternative urinalysis tube with only two chambers. The main chamber 12 which is larger and the smaller chamber 9, which contains the test strip 6 with all its components as previously described with the addition of 6h for additional chemistry tests if so desired when available. The strip is likewise built in and attached by the use of the adhesive portion 6a into the internal arc-like wall of the test strip chamber 9 to effect the optimal visual analysis of the different color changes that may occur in the various chemical reagent components 6b, 6c, 6d, 6e, 6f, 6g, and 6h. This particular urinalysis tube design having two chambers only is designated wit numeral 29, and in this case there is no chamber for specific gravity and there is no thin double walled flattened cul-de-sac-like sedimentation and microscopic examination area, thereby no allowance for a protective sheath at the bottom part of the tube is provided. The wall 51 separates the main chamber 12 from the test strip chamber 9. Also shown in this figure are several equidistantly spaced openings 52.

In FIG. 14 the wall 51 and the tracing of the upper portion of the opening 52 are illustrated in top view of the urinalysis tube of this particular type.

In FIG. 15 there is shown the left hand 58 of the tester holding in an elevated position, the tube of FIG. 1 designated as 1 with cap 2 properly engaged; the specific gravity chamber as well as the test strip chamber are clearly shown. In this fashion, the tester achieves an advantage of clearly being able to read the specific gravity of the particular urine specimen by matching the widest diameter of the flotation component 4 against the nearest hair-like calibration of the imprinted or etched specific gravity calibration 5. Color changes occurring internally in the various segments of the test strip designated for the various tests, can visually be analyzed according to a color chart specific to each of the different chemistry tests involved in the said test strip. The analysis of the color changes and the results that may be derived from these tests can be done without exposure of the test strip to the outside environment. The thin flattened double walled cul-de-sac-like sedimentation area 8 with its gridded microscopic area 13 is shown exposed without the covering sheath 3. By rotating the same tube to a position where the label of the tube and the main chamber face the tester, it is possible to observe and grade the clarity, turbidity, haziness, or cloudiness of the urine specimen being tested; he can also report the color intensity as well as the kind of urine coloration of the particular urine specimen. Urine coloration is significant to the determination of normality or pathological states of the patient whose urine is under urinalysis testing. The protective sheath 3 shown on the table top of the laboratory is still detached from the lower portion of the flattened microscopic sedimentation area. Just before centrifugation, the sheath can be optimally engaged to protect the said flattened area in order to prevent the accidental breakage of the latter during the process of centrifugation and prior to microscopic examination of the urine specimen. Also shown is the urine test tube rack 55 with the consecutively numbered vertically aligned urinalysis tubes containing the specimen from various patients. Area 54 of each tube label is for designating the individual test numbers of each particular specimen. The tube rack has a series of equidistantly spaced upper openings 56 coordinated with a series of aligned lower openings 57 to accommodate each individual urinalysis tube in a vertical manner. The tube rack shown resting on table top 100 prevents the accidental breakage of the tubes during the systematic performance of urinalysis testing.

Figure 16:
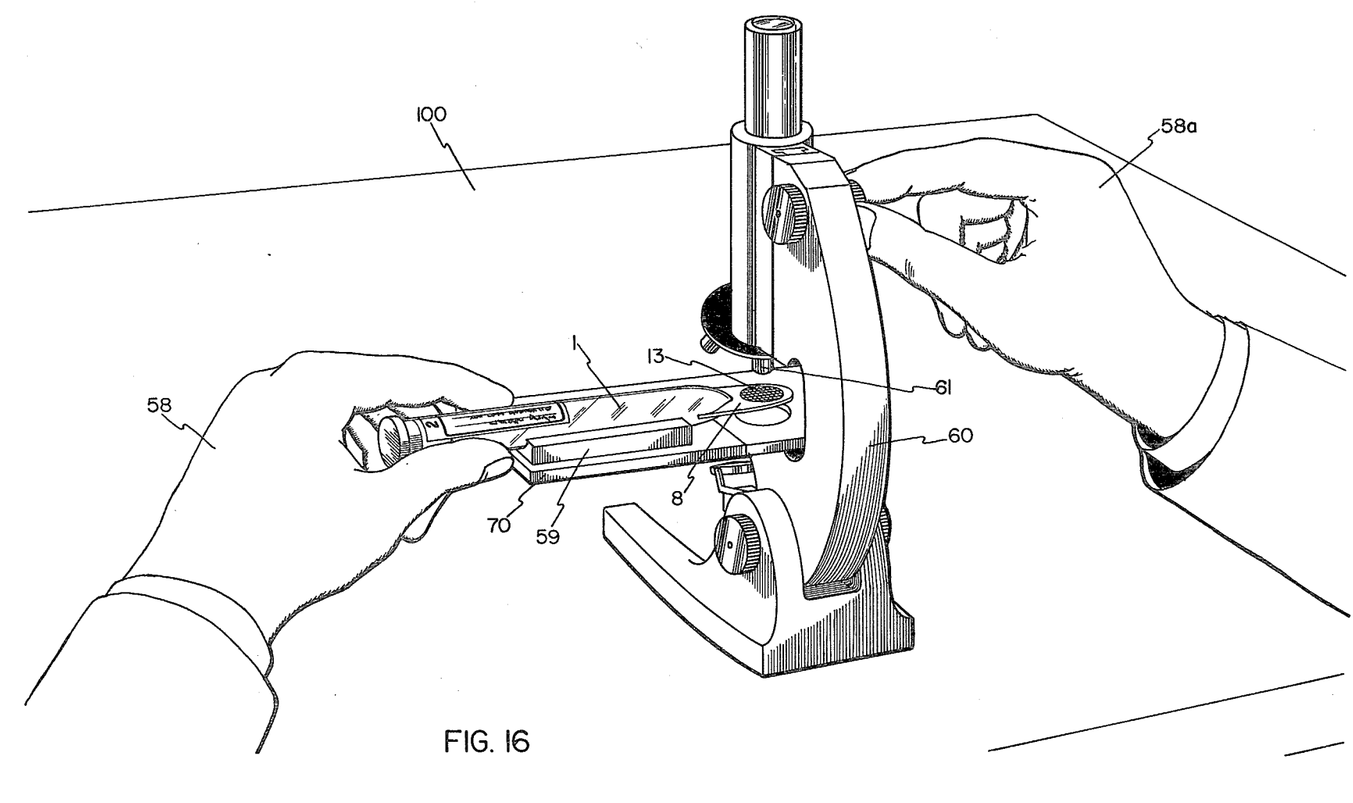
FIG. 16 is a reduced perspective view of the same present invention as seen in FIG. 1 wherein the said urinalysis tube is shown in proper longitudinal alignment in relation to the microscope also shown in perspective view accentuating a clarified illustration on how the gridded microscopic area of the double walled thin flattened cul-de-sac-like bottom section of the device is being centered under the lens of the microscope ready for microscopic examination of the urine sediments.

In FIG. 16 we see in perspective, a view of a microscope 60 being adjusted by the right hand 58a of the technologist. The urinalysis tube is shown in a horizontally adjusted position held by the left hand 58 of the tester and is placed firmly upon the arc-like cradle portion of 59 which is the tube rest component of structural extention 70 that is firmly attached to the microscope stage. It is important to note that at this point, the urinalysis tube has already been properly centrifuged, and that the urine sediments have already settled at the thin flattened double walled cul-de-sac-like sedimentation area so that the microscopic examination of the sediment can be performed. The supernatant fluid of the centrifuged urine specimen has already been decanted from the urinalysis tube, so as to prevent the undesired fluidic inter-action of the supernatant fluid against the settled urine specimen thus diminishing the unwanted swirling of the formed elements of the sediment which can interfere with the visual microscopic indentification and estimation of the important constituents of the sediment under study. The gridded microscopic area of the flattened double walled sedimentation area is shown centered under the lens 61 of the focused microscope 60. The microscope as well as the attached specimen stage extension 70 including tube rest 59 and the horizontally placed urinalysis tube are altogether steadily kept in place by table 100 to allow accurate microscopic examination.

HOW THE INVENTION IS USED

1. Align the new compact sanitary urinalysis tubes in consecutive order in the urinalysis tube rack 55, after numbering each tube correspondingly to the individual specimens to be tested. Be sure that all the information on each urinalysis tube properly matches the information on each urine specimen label attached to each particular specimen container. In this manner the paient's name, hospital number, doctor, room number and the test number of each of the tubes can be correctly matched with the right specimen containers before the testing procedure commences.

2. Open the batch of the vertically aligned tubes that have already been numbered in the rack by disengaging the cap from each one of the tubes and laying the caps in an orderly fashion beside each tube.

3. Open each urine container with the urine specimens to be tested and lay aside the corresponding covers beside each corresponding container.

4. Slowly pour the urine specimen from each specimen container into the correspondingly correct urinalysis tube, filling the three chambers such as the main chamber 12, the specific gravity chamber 10, and the test strip chamber 9 up to some approximate level such as is illustrated by numeral 53 of FIG. 1. Having the proper amount of urine in the main chamber will insure that after centrifugation, within a certain optimally acceptable time-frame, enough sediment material will be collected at the sedimentation area 8a of FIG. 5 for the proper examination through microscopic area 13 of FIG. 4; also with this specimen content level, seen in both the specific gravity chamber 10 and the test strip chamber 9, there will be enough urine sample to activate the specific gravity flotation component for the determination of the correct specific gravity of the particular urine specimen as the said flotation component is matched by the tester against the specific gravity calibrations imprinted or etched at the external surface of the specific gravity chambers as shown in FIG. 1; also, at this specimen level, the test strip chamber will have enough urine specimen to effect the necessary chemical reactions in the test strip so that the various color changes for the quali-quantitative determination of the different chemical constituents in each particular urine sample can be brought about.

5. Cover each of the compact sanitary urinalysis units with each of the corresponding caps in consecutive order as soon as the desired individual specimens have been poured in respectively to each tube. Then perform the emergency routine urinalysis first before proceeding to complete the rest.

6. With the properly numbered urinalysis report test slip, write the correct results regarding certain visual observations on each particular urine specimen such as the kind and intensity of color, as well as the state of clarity, turbidity, haziness or cloudiness of the said urine sample. This visual investigation can be done by the tester by merely looking through the transparent glass or plastic framework of the new urinalysis tube. Lifting each respective tube with the left hand as illustrated in FIG. 15, the tester may rotate the tube so as to align the specific gravity chamber to his best field of vision. It is preferable that during the determination of the specific gravity, the urinalysis tube of the instant invention be held in a vertical position as illustrated again in FIG. 15 so that the flotation component 4 will be free to float to its highest point of buoyancy depending upon the specific gravity of the urine being tested. To keep the flotation component from adhering onto the walls of the specific gravity chamber, gently shake the tube to allow the flotation component to have freedom in its upward motion to attain its highest flotation capabilities, so that the specific gravity of the urine into which the said component is immersed can be properly and accurately determined by matching the largest diameter of the said flotation component 4 against the specific gravity calibration 5. Afterwards, report the specific gravity of that particular urine sample on the proper specific gravity sector of the laboratory slip.

7. By rotating the same urinalysis tube so that the test strip chamber optimally faces the best field of vision of the tester, it is possible to visually observe the various color changes in the different chemistry reagent test segments of the test strip in order that he may be able to accurately note and report the quali-quantitative concentrations of such tests as the ph factor, protein, glucose, hemoglobin, ketones and bilirubin in the proper sections of the laboratory test report slips.

8. In case the tester is using a series of compact sanitary urinalysis tubes having the special caps containing the built-in powdered staining agents, he simply must turn the rotatory component of the cap to approximately 180 degrees from its original position with his right hand, while supporting the respective tube firmly with his left thus releasing the powdered staining agent into the larger main chamber of the said urinalysis tube. Performing the same procedure to each and every tube and cap, he can then place the various tubes containing the multiplicity of individual specimens inside the slots of an ordinary centrifuge in a balanced fashion, because the dimension of the urinalysis tubes is preferably made within an optimally acceptable diameter that can perfectly fit inside the regular slot diameter of the commonly used urine centrifuge equipment. It is a must that, before centrifuging each urinalysis tube, the protective sheath 3 as illustrated in FIGS. 1, 6, and 7 are correctly engaged in the optimal covering protective position in order that breakage of the thin double walled flattened cul-de-sac-like sedimentation and microscopic area can be prevented. During centrifugation, the immersed stain inside the main chamber of the urinalysis tube can gradually react with the formed elements of each of the urine specimens respectively contained in the corresponding urinalysis tubes. This staining reaction is accelerated by the centrifugal force attained during the process of centrifuging, so that, by the time the sediments are collected into the respective sedimentation and microscopic area of each urinalysis tube within a certain pre-calculated time-frame and r.p.m. centrifugation speed, better staining of the formed constituents that are found in each particular urine specimen can be achieved, thereby bringing forth better visual contrast among the said formed elements for greater accuracy of microscopic identification and estimation. However, if the tester is not using the special cap having the built-in staining agents, and is just using the plain caps for covering the urinalysis tubes, he does not have to perform the act of rotating the caps in a 180 degree fashion because there is no staining agent to be released into the main chamber of the urinalysis tube. Microscopic examination of the sediments can still be performed, but not with greater visibility contrast among the formed elements of the sediment as it would be if powdered staining agents were used.

9. After centrifugation of the batch of compact sanitary urinalysis tubes, the tester can align the said tubes back to the test tube rack in consecutive order.

10. Remove each cap from each tube and decant the supernatant portion of the urine specimen leaving the sediments with a minimal amount of fluid at about the level of 101 which represents the pre-tested optimal level of supernatant fluid necessary to bring about the best dilution factor for the sediment to be mixed. Before decanting the supernatant portion of the urine, the protective sheath must be removed from its covering position so that the tester can see the pre-selected line or level 101 marked at the external part of the lower portion of the tube as shown in FIG. 15. By gently agitating the mixture of the leftover supernatant fluid and the sediment that has collected inside the thin double walled flattened cul-de-sac-like sedimentation and microscopic area, a uniform distribution of the formed elements of the urine sediment suspended in the minimal amount of leftover supernatant fluid can be attained.

11. Close the tubes with each corresponding cap and line them up in a horizontal manner in consecutive order just before microscopic examination of the specimen. By leaving the tubes in the horizontal position, part of the supernatant and sediment mixture can gravitate via the sloping area 1a of FIGS. 4, 5, 6, and 7, allowing the leftover sediment and supernatant mixture to settle in the thin flattened double walled cul-de-sac-like sedimentation area so that the microscopic analysis and estimation of the various formed constituents can be accurately accomplished by the tester through the gridded portion 13 when the said tube has been properly aligned in a horizontal position as shown in FIG. 16.

12. Microscopic examination of the series of urine specimens from various patients can be done one after another in a consecutive order as is shown in FIG. 16 wherein the compact sanitary urinalysis tube is placed in a horizontal position onto the arc-like cardle portion of 59, adjusting the location of the gridded microscopic section in a horizontal fashion relative to the microscope and especially aligned to the field of focus of the microscope lens 61. Although the thin flattened double walled cul-de-sac-like sedimentation and microscopic area is a little bit elevated above the microscope stage because of its central location with respect to the axis of the urinalysis tube, it has been properly experimented that in this elevation, both the low power and high power microscopic examination of the sediments, using the high power and low power lenses of the microscope, respectively, can be accomplished by simply adjusting the height of the microscope stage relative to the height of the respective lenses thereby focusing the gridded area 13 of the urinalysis unit.

13. Report all data pertaining to the microscopic examination of each specimen's sediment onto the corresponding laboratory report slip that has been correspondingly numbered to match each respective tube.

14. Since the new urinalysis tube is made to be disposable, then, after achieving the necessary verification as to the completeness and accuracy of reporting on the respective report slip, the whole compact sanitary urinalysis unit can be discarded into a sanitary container with liquid antiseptic agents or discarded into a sanitary sterilization compartment supplied with ultraviolet energy or equipped with disinfecting heating capabilities.

15. Other additional testings such as the quantitative determination of glucose by the clinitest method as well as other important supplemental tests can be done afterwards utilizing the urine samples contained in the respective glass, plastic or paper containers as previously mentioned.

The just described usage for the compact sanitary urinalysis tube has been centered upon the various steps encountered in the performance of routine urinalysis testings wherein all the component parts such as the special cap with built-in staining agent, the larger main chamber, the specific gravity chamber, the test strip chamber, the thin flattened double walled cul-de-sac-like sedimentation and microscopic area and the protective sheath material, are all integrated into one whole unit. However, in the alternative embodiments such as the one incorporating only the three chambers such as the main larger chamber and the two longitudinal smaller chambers such as the specific gravity chamber and the test strip chamber, without the special cap, and without the thin flattened double walled cul-de-sac-like sedimentation and microscopic area and its corresponding protective sheath material, as well as the other alternative embodiment that utilizes only two chambers such as the main larger chamber and the smaller longitudinal test strip chamber, the procedure for usage as described collectively in the variously enumerated steps can only be partly adapted.

It must be understood that with more advancements in the field of clinical laboratory medicine, it is possible to apply the present invention in coordination with an electronic image scanner leading to a faster analysis and estimation of the formed elements of the urine sediment without the use of the ordinary laboratory microscopes. The only requirement would be the mere insertion of the thin flattened double walled cul-de-sac-like sedimentation and microscopic area into the electro-optical system of the electronic image scanner, and within a few seconds, the accurate microscopic readings can be printed in the correct report slip.

It is to be clarified that in the analysis and estimation of the formed elements of the sediment by the microscopic method, the use of the gridded microscopic form imprinted at the top face of the thin flattened double walled cul-de-sac-like sedimentation and microscopic area may be eliminated, and the correct estimation of the concentrations of the formed elements in the sediment may be done by the use of specially gridded microscope eyepiece. Or else the grid-form may also be printed or etched at the underside of one of the walls of the flattened sedimentation area thus achieving better focusing between the grid-form and the formed elements of the sediment due to greater proximity between each other.

Emphasis is made here that although the present invention stresses upon a built-in chemistry reagent strip, it is also possible to just drop the chemistry test strip into the corresponding chemistry test strip chamber, which can easily be achieved properly, especially in the embodiment that utilizes only the two chambers.

Since some possible color changes may occur in the chemistry reagent test strip because of the use of the clear transparent framework of the urinalysis tubes allowing excessive entrance of light energy waves or photons that may react with the sensitive chemical constituents of the said built-in chemistry reagent strip, it is of utmost importance to pack the new urinalysis units inside containers having light filtering capabilities such as a darkly colored glass or plastic material, unless the chemistry test strip can otherwise be made stable enough and non-light sensitive.

Manufacturing a transparent special two-component cap having some powdered staining agent will make it easier for the tester to release the stain into the main chamber. Although the instant invention has been properly described and drawn in the different embodiments, some other additional modifications, designs and applications of the invention which will be obvious to those skilled in the art, are herewith included within the spirit and the scope of the invention, whether they may be for current use or for future use, as long as the said other designs, modifications and applications are within the perimeters of the present invention as applied for.

I claim:

1. A container for performing routine urinalysis tests comprising:

a large main longitudinal chamber for a urine specimen, said chamber circumscribed by a curved wall segment and a flat wall segment, said curved wall segment and said flat wall segment curved inwardly near an end of the chamber to form a narrow open throat extending into a end cul-de-sac-like chamber;

a pair of longitudinal extending smaller chambers adjacent each other, said chambers circumscribed by a curved wall segment, and said flat wall segment and a partition wall segment between said pair of longitudinal extending smaller chambers having vertically extending spaced apart apertures therein, said curved wall segment curved inwardly near an end thereof toward and joining said flat wall segment near an end thereof to form curved bottom ends for said smaller chambers, one of said smaller chambers being calibrated to the equivalence of the routinely accepted specific gravity hydrometer and including a flotation component therein for determining the specific gravity of a urine specimen contained in said smaller chamber, the other smaller chamber containing a chemical reagent strip to test the quali-quantitative chemical constituents of said urine;

said flat wall being non-porous to prevent the intermingling of urine in said main chamber and said pair of smaller chambers, said urine in said smaller chambers intermingled by passing through said vertically extending apertures in said partition wall;

said end cul-de-sac-like chamber intergral with said main chamber and having parallel flat walls, curved side walls, and a curved end wall to define a narrow flat chamber to accommodate urine sediments said end cul-de-sac-like chamber having spaced horizontal and vertical lines to aid in the microscopic analysis of a urine specimen;

a supporting and protecting rubber sheath surrounding the end cul-de-sac-like chamber;

indicator means on the inwardly curved portions of said curved wall segment of said flat wall segment near said open throat for indicating the proper level of supernatant fluid to be retained in said main chamber for mixing with sediments in said end cul-de-sac-like chamber; and a transparent cap for said container, said cap having a chamber therein for storing a powdered stain and means for dispensing said powdered stain into said main chamber and said means comprising a rotatable portion having a top wall, a side wall, and downwardly slanting bottom walls terminating in an off-set aperture, and a stationary portion having an offset aperture therein and having an indented side wall mateing with a plurality of protrusions near an end of said large longitudinal chamber whereby said stationary portion is locked to said main chamber whereby the contents of said chamber in said cap may be dispensed into said larger chamber by rotating the rotary portion of said cap to align said offset apertures with each other whereby the contents of said chamber of said cap will gravitate into said main chamber.

* * * * *